United States Patent
Le-Khac

(10) Patent No.: US 7,357,909 B2
(45) Date of Patent: Apr. 15, 2008

(54) PROCESS FOR PRODUCING HYDROGEN PEROXIDE

(75) Inventor: Bi Le-Khac, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 27 days.

(21) Appl. No.: 11/476,343

(22) Filed: Jun. 28, 2006

(65) Prior Publication Data

US 2008/0003175 A1    Jan. 3, 2008

(51) Int. Cl.
*C01B 15/029* (2006.01)
*C07D 301/12* (2006.01)

(52) U.S. Cl. ..................... 423/584; 549/523
(58) Field of Classification Search .............. 423/584
See application file for complete search history.

(56) References Cited

U.S. PATENT DOCUMENTS

| | | | |
|---|---|---|---|
| 3,489,663 A | 1/1970 | Bayer et al. | 204/59 |
| 4,335,092 A | 6/1982 | Dalton, Jr. et al. | 423/584 |
| 4,410,501 A | 10/1983 | Taramasso et al. | 423/326 |
| 4,428,923 A | 1/1984 | Kunkel et al. | 423/588 |
| 4,666,692 A | 5/1987 | Taramasso et al. | 423/326 |
| 4,668,273 A | 5/1987 | Haase | 71/67 |
| 4,772,458 A | 9/1988 | Gosser et al. | 423/584 |
| 4,833,260 A | 5/1989 | Neri et al. | 549/531 |
| 5,236,692 A | 8/1993 | Nagashima et al. | 423/584 |
| 5,846,898 A | 12/1998 | Chuang et al. | 502/181 |
| 5,961,948 A | 10/1999 | Wanng.ang.rd | 423/584 |
| 5,965,476 A | 10/1999 | Balducci et al. | 502/67 |
| 6,168,775 B1 | 1/2001 | Zhou et al. | 423/584 |
| 6,284,213 B1 | 9/2001 | Paparatto et al. | 423/403 |
| 6,375,920 B2 | 4/2002 | Fischer et al. | 423/584 |
| 6,387,346 B1 | 5/2002 | Bertsch-Frank et al. | 423/584 |
| 6,524,547 B1 | 2/2003 | Nyström et al. | 423/588 |
| 6,630,118 B2 | 10/2003 | Pararatto et al. | 423/584 |
| 6,649,140 B2 | 11/2003 | Paparatto et al. | 423/584 |
| 2003/0215383 A1 | 11/2003 | Escrig et al. | 423/584 |
| 2004/0151658 A1 | 8/2004 | Escrig et al. | 423/584 |
| 2005/0025697 A1 | 2/2005 | Rueter et al. | 423/584 |
| 2005/0201925 A1 | 9/2005 | Le-Khac et al. | 423/584 |
| 2005/0209396 A1 | 9/2005 | Calhoun et al. | 524/556 |
| 2007/0086940 A1* | 4/2007 | Le-Khac et al. | 423/584 |

FOREIGN PATENT DOCUMENTS

| | | |
|---|---|---|
| EP | 0 498 166 A1 | 1/1992 |
| GB | 1 546 809 | 12/1976 |

OTHER PUBLICATIONS

K. Se et al., *J. Polym. Sci. Part A: Polym. Chem.* 35(7) 1997) 1219, no month.
Y. Kirsh, *Prog. Polym. Sci.* 11 (1985) 283, no month.
F. Helfferich, *Ion Exchange*, McGraw-Hill Book Company, Inc. (1962) 47, no month.

* cited by examiner

Primary Examiner—Wayne A. Langel
(74) Attorney, Agent, or Firm—Yuanzhang Han

(57) ABSTRACT

A process for producing hydrogen peroxide from hydrogen and oxygen in the presence of a noble metal and a cationic polymer comprising a halogen-containing anion is disclosed. The cationic polymer improves hydrogen peroxide yield, and it can be easily recycled.

18 Claims, No Drawings

US 7,357,909 B2

PROCESS FOR PRODUCING HYDROGEN PEROXIDE

FIELD OF THE INVENTION

The invention relates to a process for reacting hydrogen and oxygen to produce hydrogen peroxide.

BACKGROUND OF THE INVENTION

Hydrogen peroxide is an important intermediate chemical useful in such applications as water treatment, pulp and paper bleaching, and organic synthesis. At present, the commercial process for producing hydrogen peroxide involves anthraquinone autooxidation (see, e.g., U.S. Pat. Nos. 4,428,923 and 6,524,547). The process requires numerous reaction and purification sections, uses a large volume of solvent, and provides a less-than-ideal yield of hydrogen peroxide.

Hydrogen peroxide can also be made by a direct reaction of hydrogen and oxygen in the presence of a suitable catalyst, particularly a noble metal catalyst (see, e.g., U.S. Pat. Nos. 4,335,092, 4,772,458, 5,236,692, 5,846,898, 5,961,948, 6,168,775, 6,284,213, 6,375,920, 6,387,346, 6,630,118, 6,649,140; U.S. Appl. Pub. Nos. 2003/0215383, 2004/0151658, and 2005/0025697). A promoter such as chloride, bromide, iodide (e.g., NaBr, HBr) can improve hydrogen peroxide yield. However, these promoters are generally soluble in the reaction solvent and their recovery is troublesome. EP 0 498 166 A1 discloses a hydrogen peroxide-producing method using a catalyst comprising a platinum group metal catalyst impregnated with an organic halogen-containing compound that is insoluble in water.

Despite these efforts, new processes for making hydrogen peroxide from hydrogen and oxygen with improved productivity and selectivity need to be developed.

SUMMARY OF THE INVENTION

The invention relates to a process for producing hydrogen peroxide from hydrogen and oxygen in the presence of a noble metal and a cationic polymer comprising a halogen-containing anion. The cationic polymer improves hydrogen peroxide yield, and it can be easily recycled.

DETAILED DESCRIPTION OF THE INVENTION

The process uses a cationic polymer. A cationic polymer is any polymer that is positively charged. The positive charge may reside in polymer's side chains or its backbone. The cationic polymer may contain ammonium, phosphonium, or sulfonium functionalities. The ammonium or phosphonium ions may be primary, secondary, tertiary, or quaternary. Polymers containing ammonium ions are preferred. More preferred are those containing quaternary ammonium ions. Most preferred are those containing N-alkyl pyridinium ions. The cationic polymer may contain other functional groups such as ether, alcohol, ester, amine, carboxylic acid, ketone, and the like, and mixtures thereof.

The cationic polymer comprises a halogen-containing anion. Preferably, is the halogen is selected from the group consisting of chlorine, bromine, iodine, and mixtures thereof. The halogen-containing anion may be a halide, oxyanion, halogen-containing sulfonate, carboxylate, phenoxide, alkoxide, halide, and the like. Suitable anions include, e.g., chloride, chlorate, perchlorate, bromide, bromate, iodide, periodate, p-bromobenzoate, 2-chloroacetate, 2,6-dichlorophenoxide, and mixtures thereof. Preferred anions are inorganic (containing no carbon). Examples of inorganic anions are chloride, chlorate, perchlorate, bromide, bromate, iodide, periodate, and mixtures thereof. More preferred anions are chloride, bromide, iodide, and mixtures thereof, and the most preferred is bromide.

There are many suitable ways for preparing cationic polymers of the invention. In one method, the cationic polymer is prepared by polymerizing a cationic monomer, preferably a vinyl-functional one. Suitable vinyl-functional cationic monomers include, e.g., N-alkylvinylpyridinium halides, N-vinylpyridinium halides, N,N,N-trialkyl-4-vinylphenylammonium halides, N,N,N-trialkylallylammonium halides, [2-(acryloxy)ethyl]trimethylammonium halides, [2-(methacryloxy)ethyl]-trimethylammonium halides, (3-acrylamido-propyl)trimethylammonium halides, N,N-diallyl-N,N-dimethylammonium halides, [2-(acryloxy)ethyl-]dimethylbenzylammonium halides, [2-(methacryloxy)ethyl]dimethyl-benzylammonium halides, and the like (e.g., U.S. patent application No. 2005/0209396). Suitable polymers can also be prepared by polymerizing cationic monomers containing phosphonium or sulfonium ions (e.g., P,P,P-trialkylallylphosphonium halides, [2-(acryloxy)ethyl] trimethylphenyl-phosphonium halides, [2-(methacryloxy) ethyl]trimethylphosphonium halides, (3-acrylamidopropyl) trimethylphosphonium halides, P,P-diallyl-dimethylphosphonium halides, [2-(acryloxy)ethyl] dimethylbenzyl-phosphonium halides, [2-(methacryloxy) ethyl]dimethylbenzyl-phosphonium halides, diallylalkylsulfonium halides, allyldialkylsulfonium halides). Copolymers may be prepared with other vinyl monomers (styrene, propylene, divinylbenzene, acrylic acid, ethyl acrylate, and the like).

In another method, a cationic polymer is made by polymerizing a monomer to form a homopolymer or a copolymer precursor; the precursor is then treated (e.g., by alkylation or protonation) with a halogen-containing compound to form the desired cationic polymer. Examples of such monomers polymerizable by addition polymerization include vinylpyridines, 4-(N,N-dialkylamino)styrenes, 5-vinylbenzimidazole, vinylquinolines, allyldialkylamines, allyldialkylphosphines, allylthioethers, (2-dialkylamino)ethyl acrylates, and (2-dialkylamino)ethyl methacrylates, and the like (see, e.g., *J. Polym. Sci., Part A: Polym. Chem.* 35(7) (1997) 1219; *Prog. Polym. Sci.* 11 (1985) 283). Polymers prepared from 4-vinylpyridine, 2-vinylpyridine, 4-(N,N-dimethylamino) styrene are preferred. Vinylpyridine polymers (homopolymers or copolymers) are particularly preferred. A polymer precursor can also be prepared by condensation polymerization, as in the reaction between a diamine and a dihalide (see, e.g., GB 1546809, U.S. Pat. No. 3,489,663) or between a diamine and an epoxide (see, e.g., U.S. Pat. No. 4,668, 273). Such a polymer precursor further reacts with an alkyl halide (ethyl bromide, methyl iodide, n-propyl chloride) or a hydrogen halide (HCl, HBr, Hl) to form the desired cationic polymer. Alkyl bromides (methyl bromide, ethyl bromide, propyl bromide, benzyl bromide) are preferred post-treatment reagents. Ethyl bromide is used in Example 1.

It is not necessary to completely convert amine, phosphine, or thioether groups to ammonium, phosphonium, or sulfonium ions. A portion of free amine, phosphine, or thioether groups (e.g., 5 to 95 mole %) may be present in the cationic polymer. The cationic polymer may be formed in the $H_2O_2$-producing reaction from a polymer precursor. For example, a crosslinked poly(vinylpyridine) and HBr may be directly added to the $H_2O_2$-producing reaction, and the desired cationic polymer is formed in situ.

The cationic polymer preferably has a number average molecular weight (Mn) of at least 2,000. More preferably its Mn is at least 5,000, most preferably it is at least 10,000.

The cationic polymer is preferably crosslinked to reduce its solubility in the reaction media. Crosslinked polymers are well known to a person skilled in the art. Divinylbenzene, for example, may be used as crosslinking agent. One example of such cationic polymer is anionic ion-exchange resins (see, F. Helfferich, *Ion Exchange*, McGraw-Hill Book Company, Inc. (1962) pp. 47-58). Anionic resins generally contain amine, substituted amine, ammonium, or substituted ammonium groups. Suitable cationic polymers may be prepared by exchanging the anion (e.g., $OH^-$) of an ammonium-containing ion-exchange resin (e.g., strong base resins available from Rohm & Haas Company) with a halide (e.g., $Cl^-$, $Br^-$) or other halogen-containing anion (e.g., $BrO_3^-$, $IO_4^-$), or by reacting an amine-containing resin (e.g., weak base resins also available from Rohm & Haas) with an alkyl halide (ethyl bromide, methyl iodide). Both gelular and macroreticular ion-exchange resins can be used. Macroreticular ion-exchange resins, which consist of agglomerates of very small gelular microspheres, have both micropores and macropores, and are particularly preferred.

The present process uses a noble metal. Suitable noble metals include gold, silver, platinum, palladium, iridium, ruthenium, osmium, rhenium, rhodium, and mixtures thereof. Preferred noble metals are Pd, Pt, Au, Re, Ag, and mixtures thereof. While any of the noble metals can be utilized, either alone or in combination, palladium is particularly desirable.

The noble metal may be essentially elemental (e.g., colloidal Pd, Pd—Au alloy), or it may be supported on a carrier. Suitable carriers include carbons, zeolites, titanias, silicas, zirconias, niobias, aluminas, silica-aluminas, titania-silicas, zirconia-silicas, niobia-silicas, clays, ion-exchange resins, and the like, and mixtures thereof. Zeolites generally contain one or more of Si, Ge, Al, B, P, or the like, in addition to oxygen. Zeolite may contain transition metals ("transition metal zeolites," e.g., titanium zeolite, vanadium zeolite). Titanium silicalite-1 (TS-1) is a titanium silicalite having an MFI topology analogous to that of the ZSM-5 aluminosilicate (see U.S. Pat. Nos. 4,410,501 and 4,666,692).

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being deposited on the carrier may be fully or partially pre-reduced. Satisfactory catalytic performance can, however, be attained without any pre-reduction. Typically, the amount of noble metal present relative to the carrier is in the range of from 0.01 to 20 wt. %, preferably 0.1 to 5 wt. %.

The noble metal or the supported noble metal of the present invention may be polymer-encapsulated. By "encapsulated," we mean that it is contained within and is surrounded by a layer of polymer. Suitable polymers and techniques for encapsulating a noble metal or supported noble metal with a polymer are described in U.S. Pat. Appl. Pub. No. 2005/0201925, the teachings of which are incorporated herein by reference. In one particular example, the noble metal or the supported noble metal is encapsulated by a cationic polymer as described above (see Example 6 below).

Oxygen and hydrogen gases are required for the process. Although any sources of hydrogen and oxygen can be used, molecular oxygen ($O_2$) and molecular hydrogen ($H_2$) are preferred. The molar ratio of hydrogen to oxygen ($H_2:O_2$) used is preferably within the range of 1:10 to 10:1. More preferably, the $H_2:O_2$ ratio is within the range of 1:5 to 5:1.

In addition to oxygen and hydrogen, an inert gas may be used. Examples of suitable inert gases are helium, argon, nitrogen, methane, ethane, propane, and carbon dioxide. Because it is cheap and readily available, nitrogen is preferred. The inert gas advantageously provides a way to keep the oxygen and hydrogen levels in the reaction mixture outside the explosive limits.

The process is performed in the presence of a solvent. Suitable solvents dilute the gaseous reactants to a level effective to allow them to safely react to form hydrogen peroxide. Suitable solvents include, for example, hydrocarbons (e.g., propane, butane, isobutane, toluene, xylenes), halogenated hydrocarbons (e.g., dichloromethane, chlorobenzene, fluorinated hydrocarbons), nitrites (e.g., acetonitrile), and oxygenated solvents. Preferably, both hydrogen and oxygen have appreciable solubility in the solvent. Oxygenated solvents are preferred. The oxygenated solvent is preferably a liquid under the reaction conditions. Suitable oxygenated solvents are water, oxygen-containing hydrocarbons (alcohols, ethers, esters, ketones, and the like), carbon dioxide, and mixtures thereof. Preferred oxygenated solvents include lower aliphatic alcohols, especially $C_1$-$C_4$ alcohols such as methanol, ethanol, isopropyl alcohol, tert-butyl alcohol, and the like, and mixtures thereof. Fluorinated alcohols can also be used. Particularly preferred oxygenated solvents are water, methanol, carbon dioxide, and mixtures thereof. When carbon dioxide is the sole solvent or a co-solvent, it is preferably a liquid or a supercritical fluid under the reaction conditions.

The process may be performed in a continuous flow, semi-batch, or batch mode. Preferably, it is performed in a continuous flow mode. The noble metal and the cationic polymer may be used in a slurry or a fixed-bed. It is preferred to operate at a total pressure within the range of 1 to 200 bars. The reaction is performed at a temperature effective to produce the desired amount of hydrogen peroxide, preferably at temperatures within the range of 0° C. to 100° C., more preferably from 20° C. to 60° C.

It may be advantageous to use an acid. Suitable acids include inorganic and organic acids, e.g., nitric acid, sulfuric acid, phosphoric acid, hydrochloric acid, hydrobromic acid, pyrophosphoric acid, acetic acid. The acid is typically added within the range of 0.1 to 1000, preferably 0.1 to 100, more preferably from 1 to 10, parts per million (ppm) based on the weight of reaction mixture.

The hydrogen peroxide produced by the process described above can be used for many applications. In one particular application, the hydrogen peroxide reacts with an olefin to produce an epoxide. Methods for conducting such a process can be found in copending application Ser. No. 11/312,036, the teachings of which are incorporated herein in by reference.

The following examples merely illustrate the invention. Those skilled in the art will recognize many variations that are within the spirit of the invention and scope of the claims.

EXAMPLE 1

Quaernized Poly(4-Vinylpyridine)

A mixture containing poly(4-vinylpyridine) resin (2% crosslinked, obtained from Aldrich, 2 g), ethyl bromide (2 g, Aldrich), and DMF (5 g) is heated to 70° C. with mixing for 1 h, then cooled to room temperature. The solid is isolated by filtration, washed with methanol, and dried in a vacuum oven at 60° C. to constant weight. The recovered solid (Additive A, 3.58 g) contains 28 wt. % Br.

EXAMPLE 2

Pd/TS-1 Catalyst

TS-1 is prepared by following procedures disclosed in U.S. Pat. Nos. 4,410,501 and 4,833,260. Spray dried TS-1 is prepared by following procedures disclosed in U.S. Pat. No. 5,965,476. A sample of spray dried TS-1 (containing 80% TS-1, 20% silica binder, calcined in air at 550° C.; 2.1 wt. % Ti, 100 g) is slurried in deionized water (200 mL). Into the slurry, an aqueous tetraammine palladium(II) dinitrate solution (containing 2.65 wt. % Pd, 3.95 g) is added. Its pH is adjusted to 7.32 with 30 wt. % aqueous ammonium hydroxide solution. The round bottom flask containing the slurry is rotated at 30 rpm in a 30° C. water bath for 30 min. The solid is isolated by filtration and the filter cake is washed three times by reslurrying it in deionized water (120 mL) followed by filtration. The solid is dried in air overnight at room temperature, and then in a vacuum oven at 50° C. for 8 h. The dried solid is calcined in an oven in air by heating it to 110° C. at a rate of 10° C./min and holding at 110° C. for 2 h, then heating to 300° C. at 2° C./min and holding at 300° C. for 4 h. The calcined solid is transferred to a quartz tube. It is treated with a gas mixture (nitrogen containing 4 mole % hydrogen, flow rate 100 mL/min) at 100° C. for 1 h, then with nitrogen gas for 1 h before it is cooled to room temperature. The solid obtained (Catalyst B) contains 0.1 wt. % Pd and 2.1 wt. % Ti.

EXAMPLE 3

Hydrogen Peroxide Production

Tests are conducted in a 450-mL multi-tube Parr reactor. Five test tubes in the reactor share the same gas phase. Each test tube has a magnetic stirring bar and all bars stir at the same rate. Test tubes 1-5 are each charged with Catalyst B. Test tubes 1, 2, and 3 are additionally charged with Additive A. The amounts of the Catalyst B and Additive A in each tube are shown in Table 1. A methanol/water mixture (9/1 by weight, 5.6 g) is added to each test tube. The reactor is then closed and flushed with nitrogen. After the reactor is heated to 30° C., it is charged with hydrogen to 100 psig, and then charged with a gas mixture (4 mole % oxygen in nitrogen) to 1400 psig. The reaction mixture in each test tube is stirred magnetically at 30° C. for 1 h before it is cooled to room temperature. The concentration of hydrogen peroxide in each solution is determined by liquid chromatography (LC). Table 1 shows that including Additive A in the process improves hydrogen peroxide yield.

It is important to point out that test results can only be compared within the same Example (e.g., Test #1-5 in Example 3). A test from one Example should not be compared with one from a different Example. For example, Test #5 in Example 3 and Test #5 in Example 4 (below) use the same catalyst, but give very different yields of hydrogen peroxide. This is because reactions are conducted in closed systems and the gas compositions in different Examples are most likely different even though the initial gas compositions are about the same. This is most likely due to the fact that different amounts of oxygen and hydrogen get consumed as reactions in different Examples proceed at different rates, as a result of different activities of catalysts employed. Furthermore, these catalysts also catalyze the decomposition of hydrogen peroxide to form water and oxygen once hydrogen peroxide is formed in a slurry. The difference in the extent of hydrogen peroxide decomposition also contributes to the difference in gas phase compositions.

TABLE 1

Hydrogen Peroxide Production

| Test | Catalyst and Additive | $H_2O_2$ (ppm) |
|---|---|---|
| 1 | Catalyst B (0.10 g), Additive A (0.0043 g) | 3020 |
| 2 | Catalyst B (0.10 g), Additive A (0.0017 g) | 1990 |
| 3 | Catalyst B (0.10 g), Additive A (0.0020 g) | 2120 |
| 4 | Catalyst B (0.10 g) | 110 |
| 5 | Catalyst B (0.10 g) | 170 |

EXAMPLE 4

Hydrogen Peroxide Production

The procedure of Example 3 is repeated except that Tubes 1 and 2 contain Additive A. Tubes No. 3 and 4 contain 2% crosslinked poly(4-vinylpyridine) resin (PVPy, obtained from Aldrich). Results appear in Table 2. It shows that polyvinylpyridine that is not treated with ethyl bromide has little or no effect on hydrogen peroxide yield.

TABLE 2

Hydrogen Peroxide Production

| Test | Catalyst and Additive | $H_2O_2$ (ppm) |
|---|---|---|
| 1 | Catalyst B (0.10 g), Additive A (0.0043 g) | 3470 |
| 2 | Catalyst B (0.10 g), Additive A (0.0043 g) | 3600 |
| 3 | Catalyst B (0.10 g), PVPy (0.0029 g) | 50 |
| 4 | Catalyst B (0.10 g), PVPy (0.0029 g) | 10 |
| 5 | Catalyst B (0.10 g) | 30 |

EXAMPLE 5

Poly(Styrene-CO-4-vinylpyridine-CO-p-styryldiphenylphosphine)

In a 1-L reactor containing a solution containing styrene (32 g), 4-vinylpyridine (5 g), p-styryldiphenylphosphine (5 g), and benzoyl peroxide (0.4 g), an aqueous poly(vinyl alcohol) solution (0.1 wt. %, 200 g) is added. After a nitrogen purge, the reactor is closed and heated to 90° C. for 4 h, followed by another 2 h at 110° C. with mixing. After it is cooled to room temperature, the solid is filtered, washed with deionized water, and dried in a vacuum oven at 70° C. for 8 h. The copolymer contains 3.4 wt. % P and 1.6 wt. % N.

EXAMPLE 6

Pd/TS-1 Ecapsulated by Quaternized Poly(Styrene-CO-4-vinylpyridine-CO-p-styryldiphenylphosphine)

A solution containing poly(styrene-co-4-vinylpyridine-co-p-styryl-diphenylphosphine) (1 g, prepared in Example 5), tetrahydrofuan (8 g), and ethyl bromide (0.3 g, Aldrich) is stirred at room temperature for 2 h, followed by 30 min. at 60° C. The excess ethyl bromide is removed by ventilation into a cold trap. To the solution, Catalyst B (2 g) is added with mixing. The liquid is removed in a vacuum oven at 50° C. The solid is ground into fine powder, washed with deionized water, and dried in a vacuum oven at 60° C. to constant weight. The recovered solid (Catalyst C, 2.4 g) contains 0.02 wt. % Br, 0.064 wt. % Pd, and 64.4 wt. % TS-1.

EXAMPLE 7

Hydrogen Peroxide Production

The procedure of Example 3 is repeated except that Catalyst C is used in Tubes 1, 2, and 5, and Catalyst B is used in Tubes 3 and 4. Each tube contains about 0.1 mg Pd. Results appear in Table 3. It shows that Catalyst C gives much higher yield in making hydrogen peroxide compared with Catalyst B.

TABLE 3

Hydrogen Peroxide Production

| Test | Catalyst | $H_2O_2$ (ppm) |
|---|---|---|
| 1 | Catalyst C (0.15 g) | 1430 |
| 2 | Catalyst C (0.16 g) | 1370 |
| 3 | Catalyst B (0.10 g) | 260 |
| 4 | Catalyst B (0.10 g) | 170 |
| 5 | Catalyst C (0.16 g) | 1400 |

EXAMPLE 8

Hydrogen Peroxide Production

Tests are conducted in a 450-mL multi-tube Parr reactor. Five test tubes in the reactor share the same gas phase. Each test tube has a magnetic stirring bar and all bars stir at the same rate. Tubes 1, 2, and 5 are charged with Catalyst C. Tubes 3 and 4 are charged with Catalyst B. The amount of catalyst in each tube is shown in Table 4. Each tube contains about 0.1 mg Pd. After an aqueous hydrogen peroxide solution (5390 ppm $H_2O_2$, 5.6 g) is added to each tube, the reactor is closed and flushed with helium. The reactor is heated to 30° C., then charged with helium to 450 psig pressure. The reaction mixture in each test tube is stirred magnetically at 30° C. for 0.5 h before it is cooled to room temperature. The concentration of hydrogen peroxide in each solution is determined by liquid chromatography (LC). Table 4 shows that Catalyst C causes little hydrogen peroxide decomposition. Catalyst B, however, decomposes about 45% hydrogen peroxide under the same conditions.

TABLE 4

Hydrogen Peroxide Decomposition

| Test | Catalyst | $H_2O_2$ (ppm) | $H_2O_2$ Decomp. (Mole %) |
|---|---|---|---|
| 1 | Catalyst C (0.16 g) | 5150 | 4 |
| 2 | Catalyst C (0.16 g) | 5310 | 1 |
| 3 | Catalyst B (0.10 g) | 2980 | 45 |
| 4 | Catalyst B (0.10 g) | 2910 | 46 |
| 5 | Catalyst C (0.16 g) | 5300 | 2 |

EXAMPLE 9

Hydrogen Peroxide Decomposition

The procedure of Example 8 is repeated except that tests are performed at 60° C. for 30 min. Results appear in Table 5. It is shown by comparing Examples 8 and 9 that hydrogen peroxide decomposition by the same catalyst is faster at higher temperature. As in Example 8, Catalyst B causes significantly faster hydrogen peroxide decomposition than Catalyst C.

TABLE 5

Hydrogen Peroxide Decomposition

| Test | Catalyst | $H_2O_2$ (ppm) | $H_2O_2$ Decomp. (Mole %) |
|---|---|---|---|
| 1 | Catalyst C (0.16 g) | 4570 | 15 |
| 2 | Catalyst C (0.16 g) | 4590 | 14 |
| 3 | Catalyst B (0.10 g) | 190 | 96 |
| 4 | Catalyst B (0.10 g) | 205 | 96 |
| 5 | Catalyst C (0.16 g) | 4520 | 16 |

EXAMPLE 10

Quarernized Poly(4-Vinylpyridine)

A mixture containing poly(4-vinylpyridine) resin (25% crosslinked, obtained from Aldrich, 2 g), ethyl bromide (2 g, Aldrich), and DMF (5 g) is mixed at room temperature for 3 h. The solid is isolated by filtration, washed with methanol, and dried in a vacuum oven at 60° C. to constant weight. The solid (Additive D, 3.58 g) contains 9 wt. % Br.

EXAMPLE 11

Hydrogen Peroxide Production

The procedure of Example 3 is repeated except that Tubes 1, 2, 3, and 4 contain Catalyst B and Additive D. Tube 5 contains Catalyst B only. Results of hydrogen peroxide formation appear in Table 6. At the end of the reaction, the solid is filtered out. The liquid samples from Tests 1 to 4 each contains <1 ppm bromide, based on X-ray diffraction elemental analysis. The result shows that there is very little bromide leaching to the solution. It is expected that such catalyst system (a noble metal and a cationic polymer having a halogen-containing anion) can be easily recycled and used repeatedly without significant loss of bromide. It is particularly useful in a fixed-bed operation.

TABLE 6

Hydrogen Peroxide Production and Bromide Leaching

| Test | Catalyst and Additive | $H_2O_2$ (ppm) | Br (ppm) |
|---|---|---|---|
| 1 | Catalyst B (0.10 g), Additive D (0.0043 g) | 1650 | <1 |
| 2 | Catalyst B (0.10 g), Additive D (0.0063 g) | 1940 | <1 |
| 3 | Catalyst B (0.10 g), Additive D (0.0071 g) | 1950 | <1 |
| 4 | Catalyst B (0.10 g), Additive D (0.0071 g) | 1770 | <1 |
| 5 | Catalyst B (0.10 g) | 600 | — |

I claim:

1. A process for producing hydrogen peroxide, which comprises reacting hydrogen and oxygen in a solvent in the presence of a noble metal and a cationic polymer comprising a halogen-containing anion, wherein the noble metal is not encapsulated by the polymer.

2. The process of claim 1 wherein the cationic polymer comprises a functionality selected from the group consisting of ammonium, phosphonium, sulfonium, and mixtures thereof.

3. The process of claim 2 wherein the cationic polymer comprises ammonium ions.

4. The process of claim 3 wherein the cationic polymer comprises N-alkyl pyridinium ions.

5. The process of claim 1 wherein the halogen is selected from the group consisting of chlorine, bromine, and iodine, and mixtures thereof.

6. The process of claim 1 wherein the anion is inorganic.

7. The process of claim 1 wherein the anion is selected from the group consisting of chloride, chlorate, perchlorate, bromide, bromate, iodide, periodate, and mixtures thereof.

8. The process of claim 1 wherein the anion is bromide.

9. The process of claim 1 wherein the cationic polymer is prepared by reacting an alkyl halide with a vinylpyridine polymer.

10. The process of claim 9 wherein the alkyl halide is an alkyl bromide.

11. The process of claim 1 wherein the number average molecular weight of the cationic polymer is at least 5000.

12. The process of claim 1 wherein the cationic polymer is crosslinked.

13. The process of claim 1 wherein the noble metal is selected from the group consisting of rhenium, palladium, platinum, silver, gold, and mixtures thereof.

14. The process of claim 1 wherein the noble metal is palladium.

15. The process of claim 1 wherein the noble metal is elemental.

16. The process of claim 1 wherein the noble metal is supported on a carrier.

17. The process of claim 1 wherein the solvent is selected from the group consisting of alcohols, ethers, esters, ketones, carbon dioxide, water, and mixtures thereof.

18. The process of claim 1 wherein the reaction is performed in the presence of an acid.

\* \* \* \* \*